(12) United States Patent
Han

(10) Patent No.: US 7,245,735 B2
(45) Date of Patent: Jul. 17, 2007

(54) EARMUFF STRUCTURE FOR HEADSET OR EAR PROTECTOR

(76) Inventor: David Han, 2F, No. 32, Lane 295, Sec. 1, Tun Hua S. Rd., Taipei (TW)

( * ) Notice: Subject to any disclaimer, the term of this patent is extended or adjusted under 35 U.S.C. 154(b) by 529 days.

(21) Appl. No.: 10/815,839

(22) Filed: Apr. 2, 2004

(65) Prior Publication Data

US 2005/0220318 A1 Oct. 6, 2005

(51) Int. Cl.
*H04R 25/00* (2006.01)
(52) U.S. Cl. .................. 381/371; 381/378; 379/430
(58) Field of Classification Search ............. 381/371, 381/370, 378, 316, 318, 320, 321; 379/430
See application file for complete search history.

(56) References Cited

U.S. PATENT DOCUMENTS 5,519,783 A * 5/1996 Kumar ..................... 381/370

* cited by examiner

*Primary Examiner*—Curt Kuntz
*Assistant Examiner*—Tuan Duc Nguyen
(74) *Attorney, Agent, or Firm*—Troxell Law Office, PLLC

(57) ABSTRACT

An earmuff structure for headset or ear protector includes two earmuff shells and two integrally injection molded speaker mounting plates that are screwed to an inner side of the earmuff shells and each has a central hole for receiving a speaker therein. The speaker mounting plates are provided at a rear surface with wall portions of predetermined heights. The wall portions on one of the speaker mounting plates are formed from outer bottom surfaces of two battery compartments formed on a front surface of the speaker mounting plate at two sides of the central hole. With the speaker mounting plates, batteries and speakers may be quickly assembled to form the earmuffs or disassembled for replacement. The wall portions on each speaker mounting plate cooperates with a foam located behind the speaker to define a space functioning like a cabinet, creating clear and high quality stereo sounds output from the speakers.

5 Claims, 6 Drawing Sheets

EARMUFF STRUCTURE FOR HEADSET OR EAR PROTECTOR

FIELD OF THE INVENTION

The present invention relates to an earmuff structure for headset or ear protector, and more particularly to an earmuff structure that includes an integrally injection molded speaker mounting plate allowing quick assembling of batteries and a speaker thereto. The speaker mounting plate is provided at a rear surface with wall portions that together with a foam located behind the speaker define a space functioning like a cabinet, creating clear and high quality stereo sounds output from the speaker in the earmuff.

BACKGROUND OF THE INVENTION

FIGS. 1 and 2 shows a conventional earmuff structure for headset or ear protector. The conventional earmuff structure includes two earmuff shells 1 and 2, battery conducting electrode plates 11 that are directly welded to a circuit board 3 fixed in each of the earmuff shells 1, 2, and two speakers 4, each of which is fitted on a considerably small speaker mounting seat 41 having two hooking heads 42 provided at two lateral sides thereof and foams 40 provided at predetermined positions. The speaker mounting seat 41 is then fixed to two lateral sides of the circuit board 3 via the hooking heads 42 that provide some extents of elasticity, so that the speaker 4 is assembled to the circuit board 3. The above assembling manner has the following disadvantages:
1. The battery conducting electrode plates 11 must be welded to the circuit boards 3 in the earmuff shells 1, 2, and the speakers 4 are assembled to the circuit boards 3 by engaging the hooking heads 42 of the speaker mounting seats 41 with two lateral sides of the circuit boards 3. It is difficult and time-consuming to proceed with the welding and the assembling of the electrode plates 11 and the speakers 4 to the circuit boards 3.
2. The earmuff shells 1, 2 have quite small interior space, and the battery conducting electrode plates 11 welded to the circuit boards 3 are very close to two sides of the earmuff shells 1, 2. It would be very inconvenient to change batteries 5 in the small space of the earmuff shells 1, 2.
3. The speakers 4 are assembled to the circuit boards 3 by very tightly engaging the hooking heads 42 of the speaker mounting seats 41 with two lateral sides of the circuit boards 3. It is uneasy to disengage the speaker mounting seats 41 from the circuit boards 3 when the speakers 4 are failed and require replacement.
4. The speakers 4 assembled to the circuit boards 3 are located in an open space in the earmuff shells 1, 3. Therefore, the speakers 4 do not output clear and high quality stereo sounds.

SUMMARY OF THE INVENTION

A primary object of the present invention is to provide an earmuff structure for headset or ear protector. The earmuff structure includes a standardized speaker mounting plate that is detachably screwed to internally threaded seats on an inner surface of an earmuff shell after a speaker is assembled to the speaker mounting plate. Therefore, the earmuff can be more quickly and conveniently assembled.

Another object of the present invention is to provide an earmuff structure for headset or ear protector. The earmuff structure includes a speaker mounting plate having wall portions projected from a rear surface thereof by a predetermined height, so that the wall portions cooperate with foams located behind a speaker mounted on the speaker mounting plate to define a space functioning like a cabinet, creating clear and high quality stereo sounds output from the speaker in the earmuff.

A further object of the present invention is to provide an earmuff structure for headset or ear protector. The earmuff structure includes a speaker mounting plate that is screwed to internally threaded seats on an inner surface of an earmuff shell without forming any projections on the speaker mounting plate. The flat and wide speaker mounting plate therefore allows convenient replacement of batteries of the earmuff.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
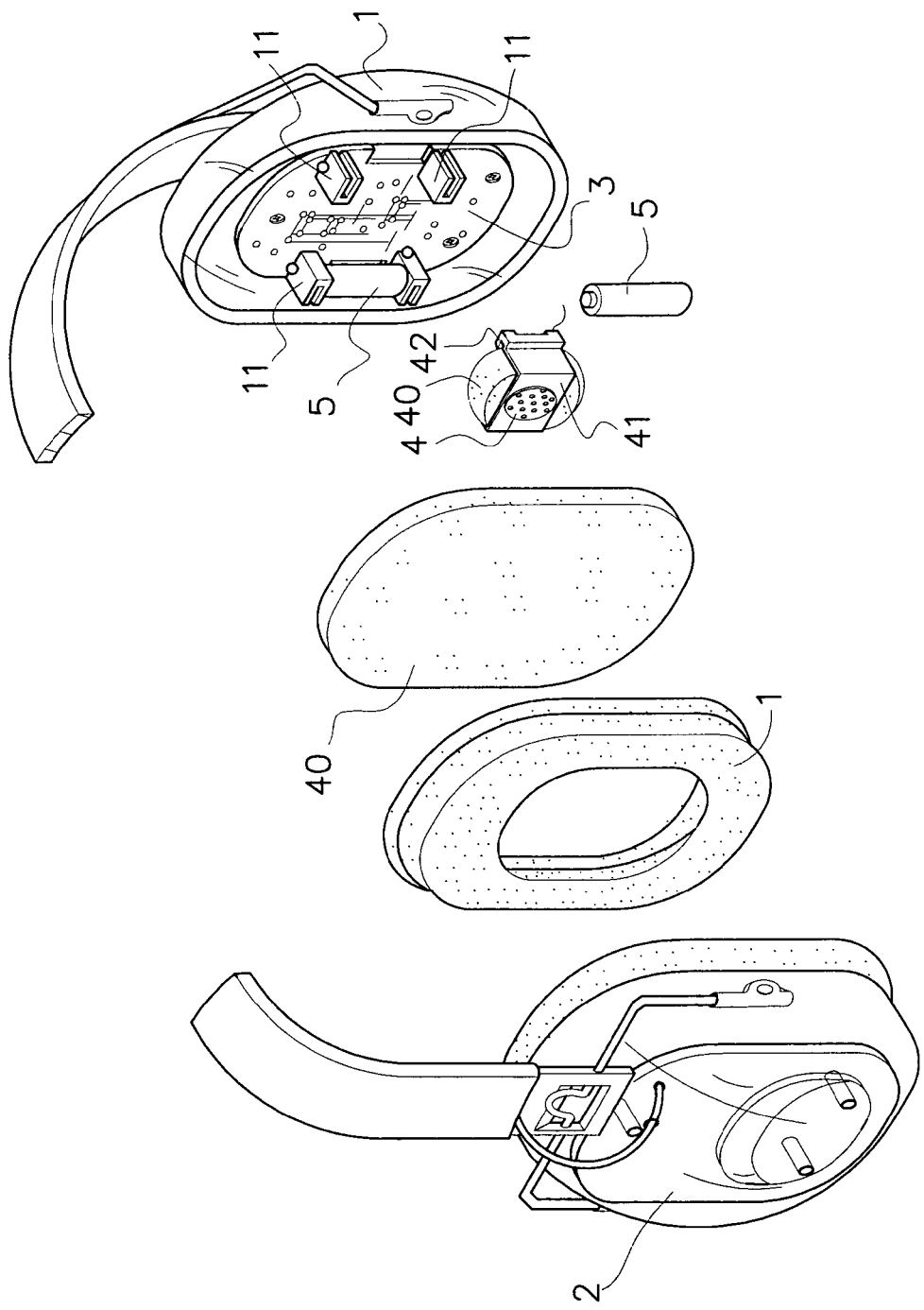
FIGS. 1 and 2 are partially exploded perspective views of a conventional earmuff structure for headset or ear protector.
Figure 2:
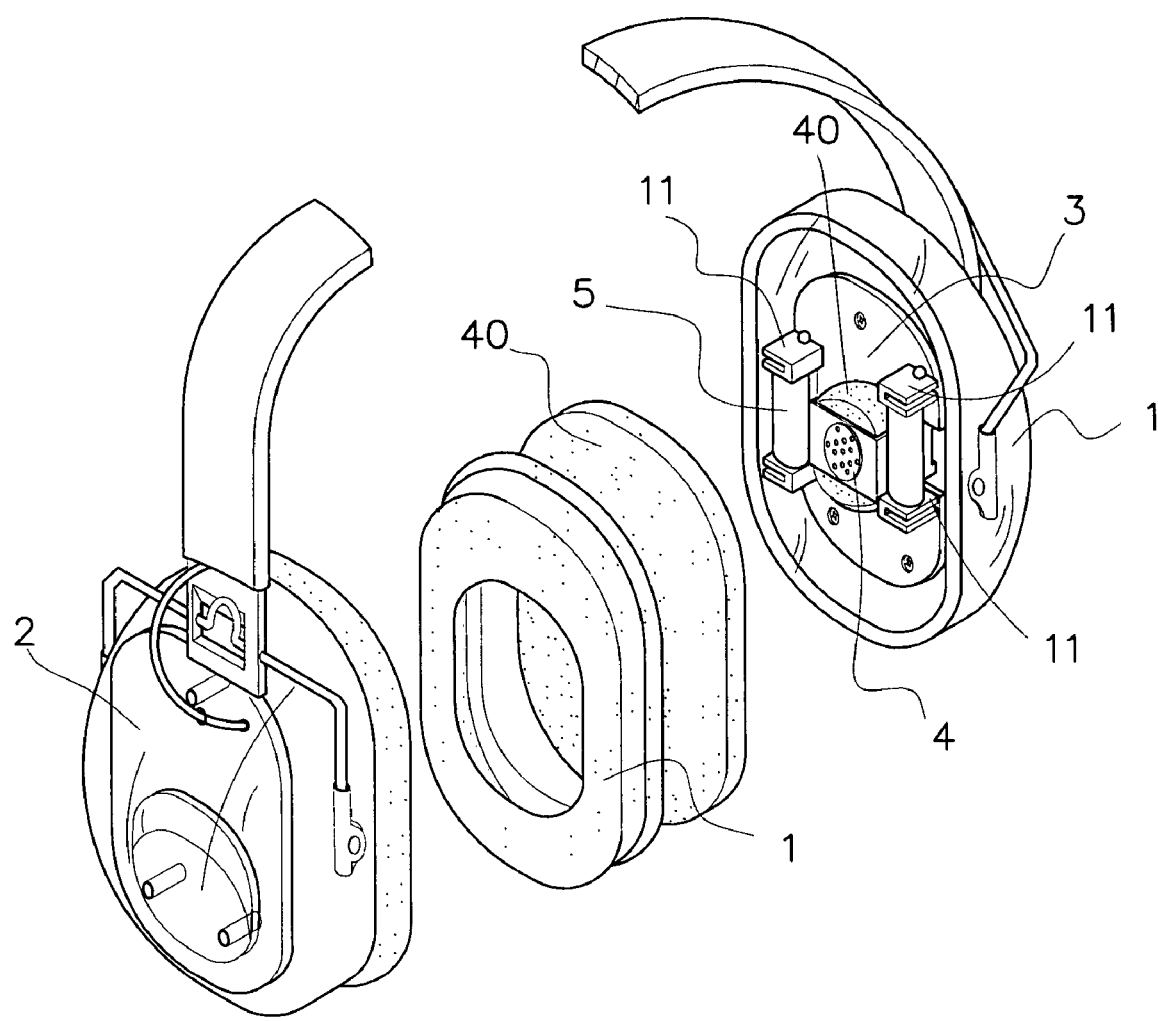
Figure 3:
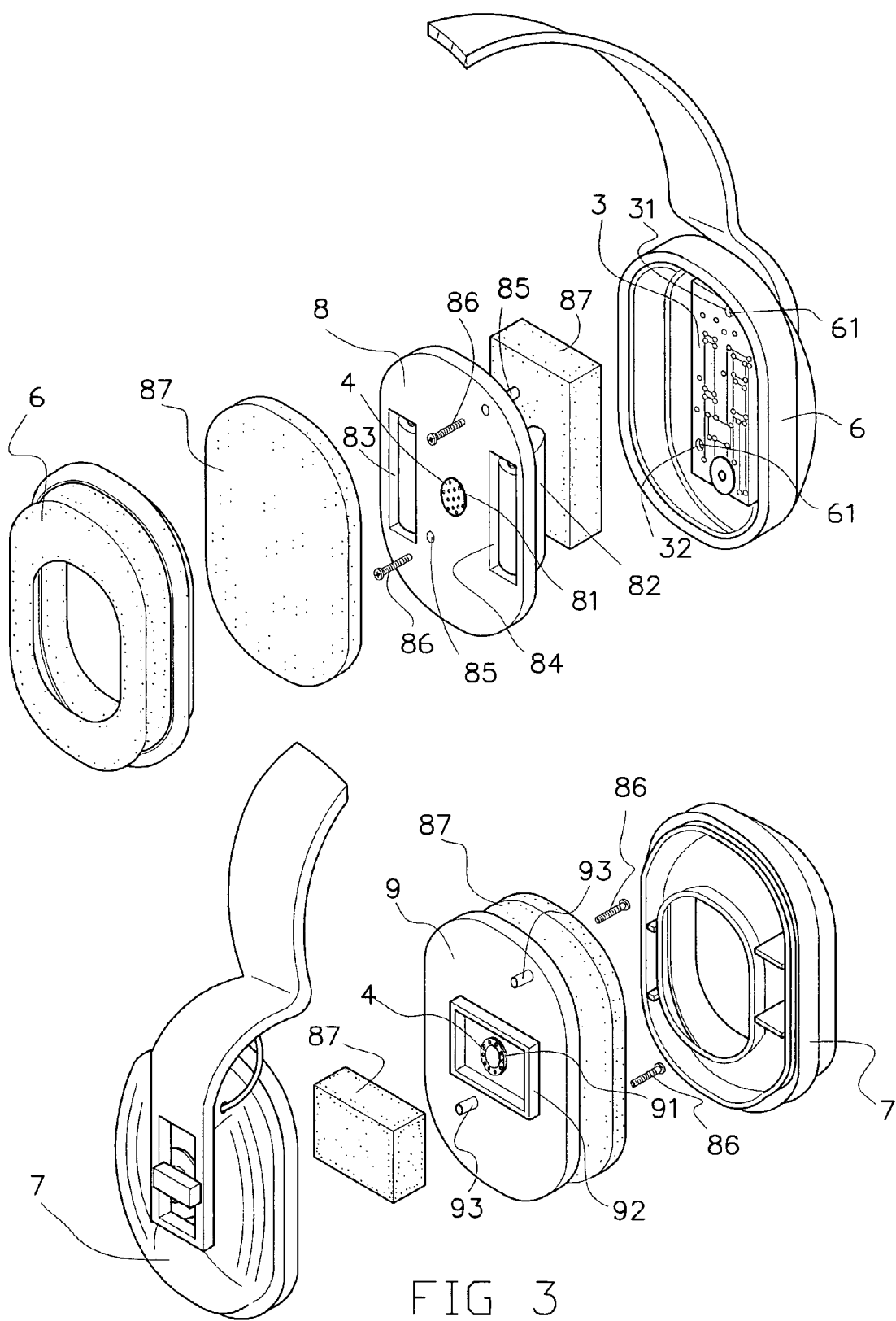
FIG. 3 is an exploded perspective view of an earmuff structure for headset or ear protector according to the present invention.
Figure 4:
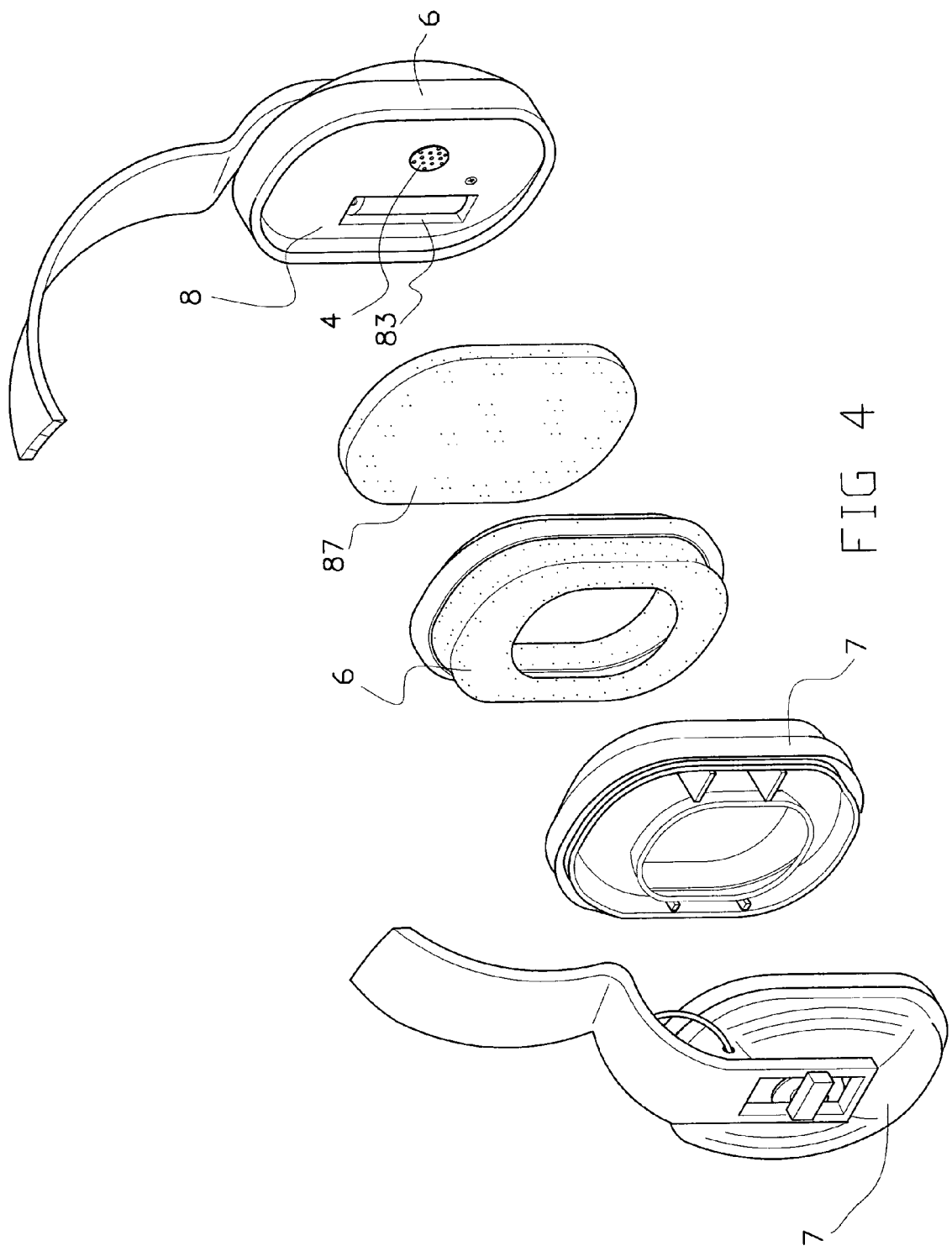
FIGS. 4 and 5 are partially assembled perspective views of the earmuff structure of the present invention.
Figure 5:
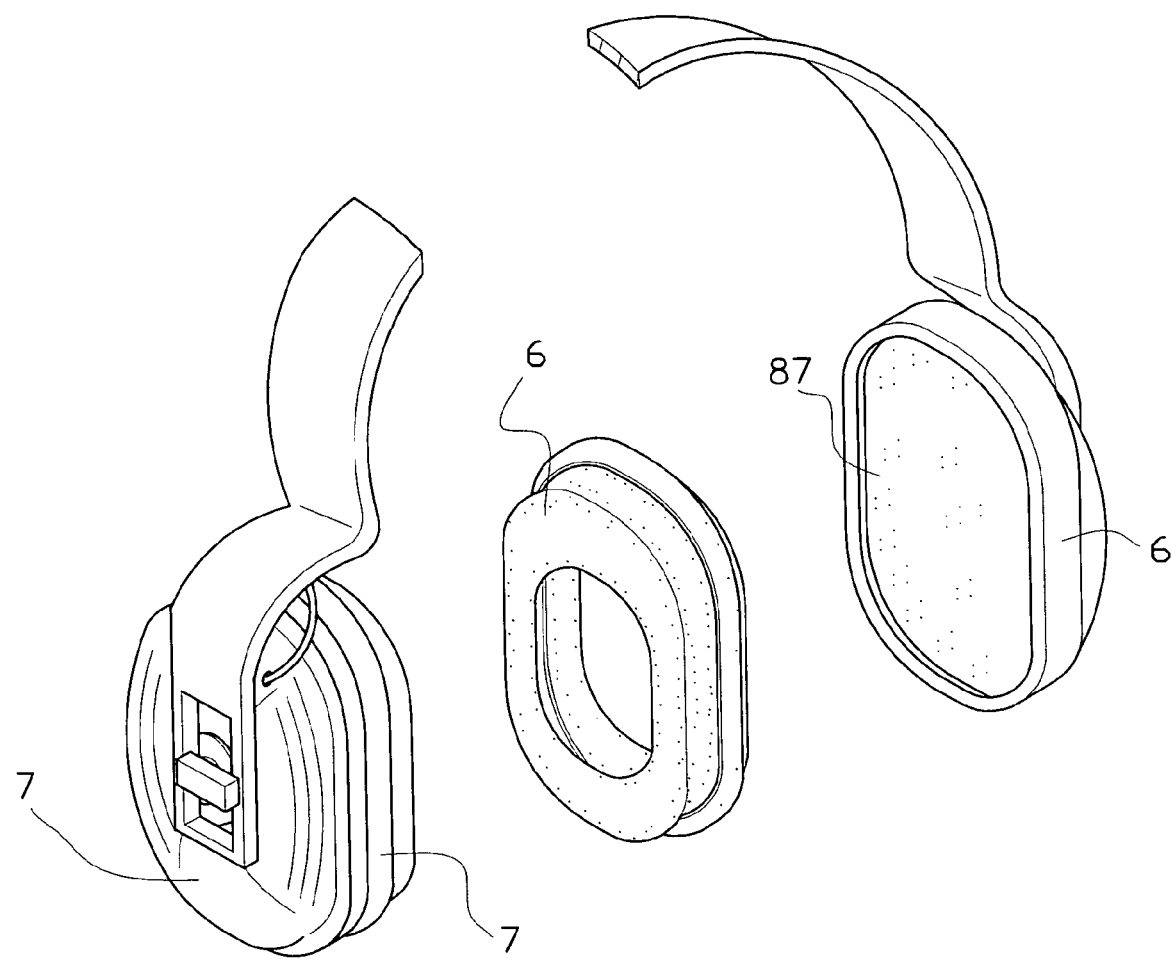
Figure 6:
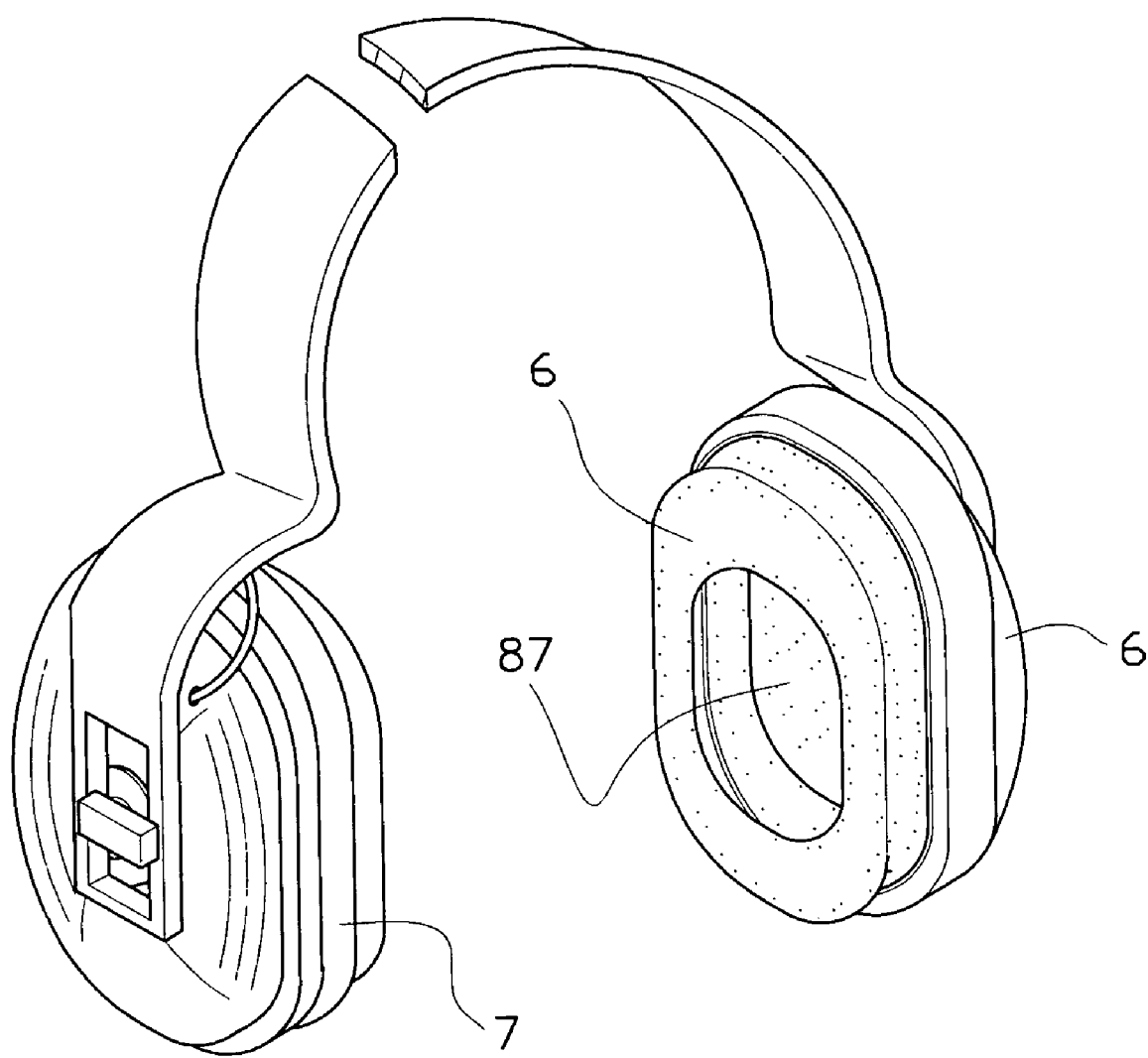
FIG. 6 is a fully assembled perspective view of the earmuff structure of the present invention.

Please refer to FIG. 3 that is an exploded perspective view of a earmuff structure for headset or ear protector according to an embodiment of the present invention, and to FIGS. 4 and 5 and 6 that are partially and fully assembled perspective views, respectively, of the earmuff structure of FIG. 3.

The earmuff structure includes two earmuff shells 6, 7, and two speaker mounting plates 8, 9, which may be integrally formed by way of injection molding and respectively have a hole 81, 91 formed at a central area thereof for receiving a speaker 4 therein. The speaker mounting plates 8, 9 are provided at respective rear side with wall portions 82, 92 having predetermined heights. The wall portions 82 on the speaker mounting plate 8 are two laterally spaced walls formed from outer bottom surfaces of two rearward projected battery compartments 83, 84 at two sides of the central hole 81.

The speaker mounting plates 8, 9 are also provided at predetermined positions with two rearward extended and internally threaded bars 85, 93, respectively, to correspond to bores 31, 32 formed on two circuit boards 3 in the earmuff shells 6, 7, so that the speaker mounting plates 8, 9 are screwed to the earmuff shells 6, 7 by screws 86 extended through the threaded bars 85, 93 on the speaker mounting plates 8, 9 and the bores 31, 32 on the circuit boards 3 into internally threaded seats 61 correspondingly formed on inner surfaces of the earmuff shells 6, 7. With these arrangements, it would be very easy to dismount the speaker mounting plates 8, 9 from the earmuff shells 6, 7 for the purpose of assembling and disassembling the speakers 4 to and from the central holes 81, 91.

The two battery compartments 83, 84 are formed on a front surface of the speaker mounting plate 8, and have battery conducting electrode plates pre-positioned therein. The battery conducting electrode plates and the speakers 4 are electrically connected to the circuit boards 3 by plugging terminals of conductors into corresponding sockets on the circuit boards 3. Therefore, it is not necessary to directly weld the battery conducting electrode plates to the circuit boards 3.

When the speaker mounting plates 8, 9 are assembled to the internally threaded seats 61 on the inner surfaces of the earmuff shells 6, 7, two foams 87 separately located behind the two speakers 4 cooperate with the wall portions 82, 92 rearward projected from the speaker mounting plates 8, 9 by predetermined heights to define two spaces around the speakers 4 to serve as two cabinets, as can be seen in FIG. 3, creating clear and high quality stereo sounds output from the speakers 4 in the earmuff shells 6, 7.

What is claimed is:

1. An earmuff structure for headset or ear protector, comprising:

two earmuff shells being provided at respective inner surface with forward projected and internally threaded seats;

a circuit board mounted in each of said earmuff shells and having bores provided thereon to correspond to said internally threaded seats on inner surfaces of each said earmuff shell; and first and second speaker mounting plates separately assembled to said two earmuff shells, and having internally threaded bars formed thereon corresponding to said internally threaded seats on inner surfaces of said two earmuff shells, wherein said first speaker mounting plate is provided at a front surface with two battery compartments located at two outer sides of one central hole of a plurality of central holes, wherein said two battery compartments formed on said first speaker mounting plate have battery conducting electrode plates pre-mounted therein; and said battery conducting electrode plates being electrically connected to said circuit boards by plugging terminals on conductors into corresponding sockets on said circuit boards.

2. The earmuff structure for headset or ear protector as claimed in claim 1, wherein said first and second speaker mounting plates are provided at respective central area with a central holes for receiving a speaker therein.

3. The earmuff structure for headset or ear protector as claimed in claim 1, wherein said first and second speaker mounting plates are provided at respective rear surface with wall portions having predetermined heights.

4. The earmuff structure for headset or ear protector as claimed in claim 1, wherein said two battery compartments formed on said first speaker mounting plate have outer bottom surfaces that rearward project to form wall portions of predetermined heights on a rear surface of said first speaker mounting plate.

5. The earmuff structure for headset or ear protector as claimed in claim 2, wherein said speakers received in said central holes on said first and second speaker mounting plates are electrically connected to said circuit boards by plugging terminals on conductors into corresponding sockets on said circuit boards.

* * * * *